United States Patent
Bunke et al.

(10) Patent No.: US 7,445,609 B2
(45) Date of Patent: Nov. 4, 2008

(54) APPARATUS FOR CONTROLLING THE DELIVERY OF MEDICAL FLUIDS

(75) Inventors: Claus Bunke, Sereetz (DE); Ralf Dittman, Lübeck-Blankensee (DE); Bernd Kaufmann, Lübeck (DE); Jens Köhne, Lübeck (DE); Jürgen Manigel, Scharbeutz-Klingberg (DE); Gerald Panitz, Klenzau (DE)

(73) Assignee: Drager Medical AG & Co. KGaA (DE)

( * ) Notice: Subject to any disclaimer, the term of this patent is extended or adjusted under 35 U.S.C. 154(b) by 350 days.

(21) Appl. No.: 11/147,305

(22) Filed: Jun. 8, 2005

(65) Prior Publication Data

US 2006/0009729 A1 Jan. 12, 2006

(30) Foreign Application Priority Data

Jul. 7, 2004 (DE) ................. 10 2004 032 814

(51) Int. Cl.
*A61M 31/00* (2006.01)

(52) U.S. Cl. ...................................... 604/65

(58) Field of Classification Search ............. 604/65–67, 604/30–34, 890.1, 891.1, 892.1, 6.11, 151; 128/DIG. 12, 13
See application file for complete search history.

(56) References Cited

U.S. PATENT DOCUMENTS

| 4,457,751 A | 7/1984 | Rodler |
| 6,572,542 B1 * | 6/2003 | Houben et al. ............ 600/300 |
| 6,599,281 B1 * | 7/2003 | Struys et al. ............... 604/503 |
| 6,631,291 B2 * | 10/2003 | Viertio-Oja et al. ......... 600/544 |
| 6,830,047 B2 | 12/2004 | Heitmeier et al. |
| 2003/0055570 A1 | 3/2003 | Ribeiro, Jr. |

FOREIGN PATENT DOCUMENTS

| DE | 30 18 641 | 6/1981 |
| EP | 1 136 090 A2 | 3/2001 |
| EP | 1 136 090 | 9/2001 |

* cited by examiner

*Primary Examiner*—Manuel A Mendez
(74) *Attorney, Agent, or Firm*—Nixon & Vanderhye PC

(57) ABSTRACT

An apparatus for medical fluid delivery is to be improved for the sake of simple monitoring of the quantity of medical fluid delivered. For attaining this object, a safety device (15) with a patient model (16) is provided, which from past values and current values of the dosage rate of the medical fluid extrapolates a future medical fluid concentration (17) and switches off the dosage unit (10) for the medical fluid if the extrapolated medical fluid concentration (17) exceeds a predetermined limit value (14).

15 Claims, 1 Drawing Sheet

APPARATUS FOR CONTROLLING THE DELIVERY OF MEDICAL FLUIDS

CROSS-REFERENCES TO RELATED APPLICATIONS

This application is based on and incorporates herein by reference German Patent Application No. DE 102004032814.5 filed on Jul. 7, 2004.

BACKGROUND OF THE INVENTION

The invention relates to an apparatus for controlling the delivery of medical fluids to a patient.

In determining the proper dosage of medical fluids, closed-loop control circuits are used to set a defined depth of hypnosis, analgesia, or degree of relaxation. As dosage devices, syringe pumps with which the medical fluids can be delivered to the patient are known. The resultant medical fluid concentration, such as the enrichment of medical fluid in the blood plasma, can be determined only by drawing blood and then examining it. In conjunction with certain medications, so-called patient models have therefore been developed, with which the medical fluid enrichment in the blood plasma can be simulated mathematically. The patient models that have been known until now apply only in conjunction with the medications associated with them and have been validated by extensive patient studies and approved by the appropriate authorities.

The so-called 3-compartment model is currently the standard patient model for the pharmacokinetics of intravenous anesthetics. It comprises one central compartment and two peripheral compartments. The division into three compartments is based on the following thought: If one begins at a single volume into which an anesthetic is applied, then two quantity courses can be determined, that is, the current quantity of anesthetic in that volume, and the quantity cumulatively eliminated from it. However, in nearly all anesthetics, the total of these two quantities does not represent the administered dose; instead, there is always a missing quantity. To compensate for this, a further peripheral volume is introduced.

One apparatus for automatic delivery of a medical fluid to a patient is known from European Patent Disclosure EP 1 136 090 A2.

The dosage rate of the medical fluid is processed in a patient model, which receives the appropriate medical fluid data from a medication database. The patient model calculates the medical fluid concentration in the body of the patient from past values for the medical fluid delivery. The calculated medical fluid concentration is compared with a set-point concentration and is supplied as a difference to a concentration regulator. The control input for the medical fluid concentration is furnished by a further regulating part, which processes a derived variable in the form of a body effect to be set (pharmacodynamics).

For monitoring the manual administration of medical fluids, the therapeutic range of the medical fluid delivery is monitored. For this purpose, it is ascertained whether the medical fluid concentration established does not exceed a predetermined tolerance range. It is left to the user how to react to any exceeding of the limit value.

For monitoring closed-loop control circuits, it is known to measure the system state with a second sensor, independent of the closed-loop control circuit, and to assess the measurement signals in a separate monitoring channel. However, a further sensor entails additional expense and, because it means a further cable connection, makes provisions for patient therapy more difficult. For the subject matter addressed here, moreover, there is no known sensor or measurement principle with which the medical fluid concentration could be determined directly in the patient's body.

BRIEF SUMMARY OF THE INVENTION

The object of the invention is to improve an apparatus of the aforementioned type with a view to simple monitoring of the medical fluid delivery.

This object is attained by providing an apparatus for varying the rate of medical fluid delivery to a patient for generating a desired body effect, having a medical fluid dosage unit for the medical fluid delivery; a patient model, which taking past values for medical fluid delivery into account calculates a current value of the medical fluid concentration in the body of the patient; a regulating device for the medical fluid delivery, which as a function of the calculated current value of the medical fluid concentration and a control input furnishes a controlling variable for the dosage unit; a body effect calculation unit, which as a function of the difference between a target value for the body effect and a measured body effect forms the control input for the medical fluid regulating device; a safety device with a further patient model, which from past and/or current values of the medical fluid delivery extrapolates a future medical fluid concentration; a shutoff means, which acts on the dosage unit and which performs a comparison of the extrapolated medical fluid concentration with a predetermined limit value for the medical fluid concentration and is embodied to output a shutoff signal to the dosage unit if the limit value is exceeded.

The advantage of the invention is essentially that for monitoring the medical fluid delivery, one additional patient model is used, with which, from past and current values of the dosage rate, a future medical fluid concentration that will become established in the patient's body is extrapolated.

In a safety device, a comparison of the extrapolated medical fluid concentration with a limit value for the maximum medical fluid concentration is performed, and if the limit value is exceeded, the dosage unit is switched off. From the extrapolation of the medical fluid concentration using a patient model, predictive monitoring values are available, in contrast to a measurement that refers only to the current instant of measurement. Thus with the patient model, medical fluid concentrations that will become established within the next minute or the next half hour can thus be calculated in advance. Critical situations can thus be recognized early, without impairing patient therapy.

Advantageous features of the invention will become apparent from the dependent claims.

Expediently, EEG measurement signals of the patient are for instance assessed as the body effect, and from this, BIS® levels are ascertained, which are a measure of the depth of hypnosis. (BIS®: Bispectral Index)

As an alternative to EEG measurement signals, muscle responses stimulated by a stimulating current or a sequence of stimuli may be assessed as the body effect. Muscle responses can be detected quantitatively for instance via a force measurement or a measurement of the electrical activity, or by means of acceleration measurement.

For extrapolating the medical fluid concentration using the additional patient model, the period of time extends expediently over a range of from 3 minutes to 30 minutes.

One exemplary embodiment of the invention is shown in the drawing and described in further detail below.

BRIEF DESCRIPTION OF THE DRAWINGS

These and other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF THE INVENTION

Figure 1:
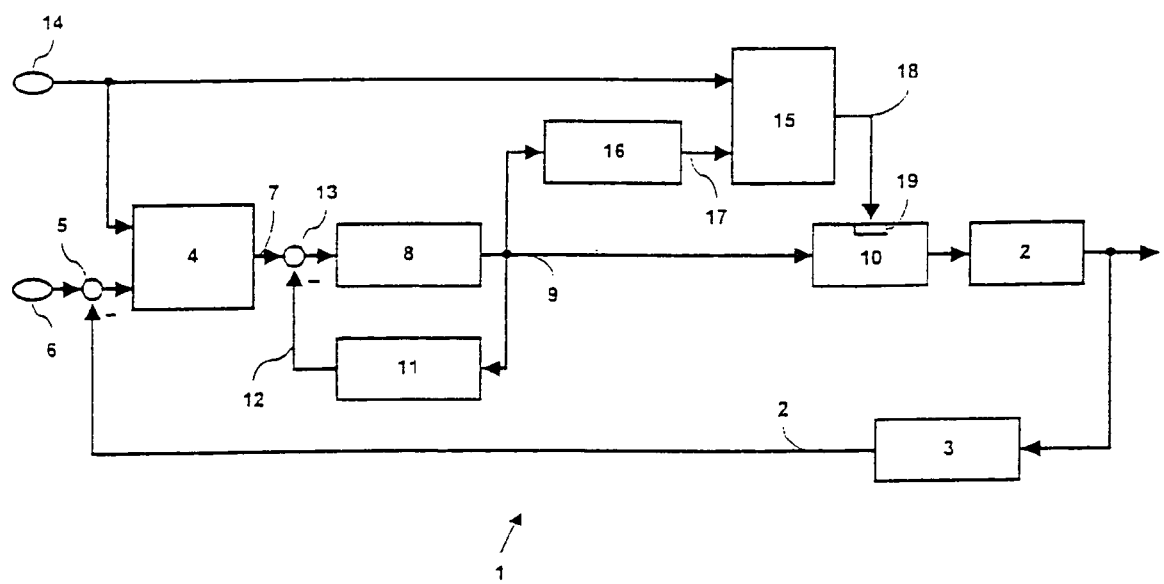
FIG. 1 illustrates a regulating apparatus according to an example embodiment of the invention.

The sole FIGURE of the drawing illustrates a regulating apparatus 1 for setting a predetermined depth of hypnosis in a patient 2. By means of a measuring instrument 3 at the patient 2, EEG measurement signals are detected, and from them a BIS® level is ascertained as an actual value for the depth of hypnosis. A target variable 6 for the BIS® level is set by a desired value setter. A body effect calculation unit 4, which receives an input variable from a comparator 5 in the form of the difference between the target BIS® value 6 and the actual BIS® value forms a control input 7 from this for the medical fluid concentration to be established, for instance the plasma concentration, in the body of the patient 2. The body effect calculation unit 4 is followed by a medical fluid regulating device 8, which furnishes a dosage rate 9 for a medical fluid dosage unit 10. The dosage rate 9 is supplied as an input variable to a patient model 11, in which the current medical fluid concentration 12 is calculated. The current medical fluid concentration is dependent on the level and duration of the medical fluid dosage. Via a comparator 13, the input of the medical fluid regulating device 8 receives the difference between the control input 7 and the calculated medical fluid concentration 12. If the calculated medical fluid concentration 12 agrees with the control input 7, the target variable of the body effect is reached; now only enough medical fluid to maintain the body effect will be administered by the dosage unit 10.

For monitoring the medical fluid concentration, a maximum medical fluid concentration 14 that must not be exceeded is predetermined at a limit value setter. This limit value is delivered to both a safety device 15 and the body effect calculation unit 4. Since in the body effect calculation unit 4 the control input 7 for the medical fluid concentration to be established is ascertained, monitoring takes place there first, using the limit value 14. If the limit value is exceeded, the dosage unit 10 is switched off. The dosage rate 9 furnished by the medical fluid regulating device 8 is supplied as an input variable to a further patient model 16, which from this extrapolates a medical fluid concentration 17 to become established in the future, on the assumption that from the present moment on, the dosage will be stopped. The patient model 16 receives both current dosage rates and dosage rates from past time periods, so that in the patient model 16, the entire administered quantity of medical fluid is available for the extrapolation.

The extrapolation may be performed over several minutes or over longer periods of time. The extrapolated medical fluid concentration 17 is compared with the limit value 14 in the safety device 15, and if the limit value is exceeded, a switch 19 which shuts off the dosage unit 10 is triggered via a signal line 18. By means of the extrapolation of the medical fluid concentration in the patient model 16, the course of the medical fluid concentration can be better predicted, making an early reaction to possible critical situations possible.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. An apparatus for varying the rate of medical fluid delivery to a patient for generating a desired body effect, having
   a medical fluid dosage unit for the medical fluid delivery;
   a patient model, which taking past values for medical fluid delivery into account calculates a current value of the medical fluid concentration in the body of the patient;
   a medical fluid regulating device for the medical fluid delivery, which as a function of the calculated current value of the medical fluid concentration and a control input furnishes a controlling variable for the dosage unit;
   a body effect calculation unit, which as a function of the difference between a target value for the body effect and a measured body effect forms the control input for the medical fluid regulating device;
   a safety device with a further patient model, which from past and/or current values of the medical fluid delivery extrapolates a future medical fluid concentration;
   a shutoff means, which acts on the dosage unit, for comparing the extrapolated medical fluid concentration with a predetermined limit value for the medical fluid concentration and for outputting a shutoff signal to the dosage unit if the limit value is exceeded.

2. The apparatus according to claim 1, characterized in that EEG measurement signals of the patient are assessed as the body effect, and from this, values are ascertained as a measure of the depth of hypnosis.

3. The apparatus according to claim 1, characterized in that electrical measurement signals of the patient are assessed as the body effect, and from this, values are ascertained as a measure of the degree of muscular relaxation.

4. The apparatus according to claim 1, characterized in that the extrapolation period for the medical fluid concentration extends over a period of from 3 minutes to 30 minutes.

5. The apparatus according to claim 1, characterized in that the medical fluid is delivered intravenously or via the respiratory system.

6. The apparatus according to claim 2, characterized in that the extrapolation period for the medical fluid concentration extends over a period of from 3 minutes to 30 minutes.

7. The apparatus according to claim 3, characterized in that the extrapolation period for the medical fluid concentration extends over a period of from 3 minutes to 30 minutes.

8. The apparatus according to claim 2, characterized in that the medical fluid is delivered intravenously or via the respiratory system.

9. The apparatus according to claim 3, characterized in that the medical fluid is delivered intravenously or via the respiratory system.

10. The apparatus according to claim 4, characterized in that the medical fluid is delivered intravenously or via the respiratory system.

11. The apparatus according to claim 1, wherein the safety device extrapolates a future medical fluid concentration based on the assumption that the dosage from that moment on is stopped.

12. The apparatus according to claim 2, wherein the safety device extrapolates a future medical fluid concentration based on the assumption that the dosage from that moment on is stopped.

13. The apparatus according to claim 3, wherein the safety device extrapolates a future medical fluid concentration based on the assumption that the dosage from that moment on is stopped.

14. The apparatus according to claim 4, wherein the safety device extrapolates a future medical fluid concentration based on the assumption that the dosage from that moment on is stopped.

15. The apparatus according to claim 5, wherein the safety device extrapolates a future medical fluid concentration based on the assumption that the dosage from that moment on is stopped.

* * * * *